(12) United States Patent
Gorin (10) Patent No.: US 8,841,574 B1
(45) Date of Patent: Sep. 23, 2014

(54) PLASMA EXTENSION AND CONCENTRATION APPARATUS AND METHOD

(71) Applicant: Georges J. Gorin, Novato, CA (US)

(72) Inventor: Georges J. Gorin, Novato, CA (US)

( * ) Notice: Subject to any disclaimer, the term of this patent is extended or adjusted under 35 U.S.C. 154(b) by 0 days.

(21) Appl. No.: 14/083,243

(22) Filed: Nov. 18, 2013

(51) Int. Cl.
*B23K 10/00* (2006.01)
*B01J 19/12* (2006.01)
*A61L 2/14* (2006.01)

(52) U.S. Cl.
CPC . *B01J 19/129* (2013.01); *A61L 2/14* (2013.01)
USPC ............ 219/121.43; 219/121.44; 219/121.54; 118/723 ME; 118/723 ER; 156/345.35; 156/345.48

(58) Field of Classification Search
CPC .............. H05H 1/46; H05H 1/30; C23F 1/08; C23F 1/12; C23F 4/02; C23C 16/505; C23C 16/511; C23C 16/513; B01J 12/002; H01J 37/32862
USPC ............... 219/121.4, 121.43, 121.44, 121.48; 118/723 R, 723 ME, 723 MP, 723 E, 118/723 ER, 725; 156/345.35, 345.36, 156/345.48, 345.43
See application file for complete search history.

(56) References Cited

U.S. PATENT DOCUMENTS

| | | | | |
|---|---|---|---|---|
| 5,658,389 | A * | 8/1997 | Matsuda et al. | 118/723 MP |
| 5,716,870 | A * | 2/1998 | Foster et al. | 438/675 |
| 6,239,553 | B1 * | 5/2001 | Barnes et al. | 315/111.51 |
| 6,497,826 | B2 * | 12/2002 | Li et al. | 216/67 |
| 6,692,649 | B2 * | 2/2004 | Collison et al. | 216/67 |
| 6,726,803 | B2 * | 4/2004 | Kondo et al. | 156/345.43 |
| 6,828,241 | B2 * | 12/2004 | Kholodenko et al. | 438/706 |
| 7,393,432 | B2 * | 7/2008 | Dhindsa et al. | 156/345.44 |
| 8,366,829 | B2 * | 2/2013 | Yin et al. | 118/719 |
| 8,622,735 | B2 * | 1/2014 | Morrisroe | 431/2 |
| 2012/0034137 | A1 * | 2/2012 | Risby | 422/186.29 |

* cited by examiner

*Primary Examiner* — Mark Paschall
(74) *Attorney, Agent, or Firm* — Kevin Roe (57) ABSTRACT

An apparatus and method to extend and concentrate a plasma from one or more plasma sources through at least one RF grounded pathway. A first embodiment of the invention involves a method to extend and concentrate a plasma. A second embodiment of the invention involves an apparatus to extend and concentrate a plasma. In some embodiments, an electrostatic rod inserted inside a RF grounded pathway assists the extension and concentration of a plasma that can treat one or more articles.

20 Claims, 12 Drawing Sheets

PLASMA EXTENSION AND CONCENTRATION APPARATUS AND METHOD

BACKGROUND OF THE INVENTION

1. Field of the Invention

This invention relates to the use of a plasma or a glow discharge for dissociating one or more gases into reactive and non-reactive ionic and reactive and non-reactive neutral species, and in particular, to extending and concentrating such a plasma.

2. Description of the Prior Art

Plasma apparatus can be divided into two broad categories, downstream or remote plasma and direct plasma. In downstream plasma, the article(s) are not immersed in the glow discharge, as it is in direct plasma. The result is a purely chemical and multi-directional process resulting in a somewhat more gentle treatment of the article(s) because high power electromagnetic waves at high frequency are not coupled through the article(s) and there is no heating from direct ion bombardment. In either type of apparatus, it is known in the art to employ some type of plasma for processing one or more article(s).

Typically, one or more reactive gases (such as air, oxygen-based gases, or halogen-based gases, including fluorine, chlorine, bromine, or other equivalent gases, as well as gas molecular compounds having one or more oxygen or halogen atoms), are used in combination with other gases, due to the highly reactive nature of the reactive gas(es) in a plasma chamber.

In the prior art, in downstream (remote) plasma processing, the problems encountered regarding the article can include: high energy photons reaching the surface of the article, electrical charges reaching the surface of the article, or a decrease in the concentration of reactive neutrals caused by diffusion of reactants throughout the entire volume of the vacuum chamber. For example, the prior art tries to remove the photons with passageways between the plasma exhaust of the plasma source and the article, where the passageway has an elbow (a bend of 90 degrees) or baffles (which increase the distance between the source and the article in a convoluted manner) to prevent photons from reaching the article. And the prior art also attempts to remove the electrical charges by two major means of recombining electrical charges in plasma, depending on the distance between the exhaust of the plasma source and the surface of the article.

The following two prior art patents, the U.S. Pat. No. 7,315,346 issued on Jan. 1, 2008 and the U.S. Pat. No. 5,814,154 issued on Sep. 29, 1998 to Gasonics International describe some of the above approaches. It is worth noting that in the U.S. Pat. No. 5,814,154 issued on Sep. 29, 1998, the first paragraph mentions what is patented in U.S. Pat. No. 7,315,346 as part of the prior art.

However, the prior art relies on the plasma parameters (i.e., dissociating power and pressure) of the plasma source in order to extend the plasma. But once the maximum power available and minimum operating pressure are reached, the prior art falls short in extending and concentrating a plasma for treating articles downstream. In view of the foregoing, what is needed is an improved method and apparatus to efficiently and selectively extend and concentrate a plasma to direct it at an article.

SUMMARY OF THE INVENTION

The present invention includes a RF grounded pathway coupled to the exhaust side of the discharge chamber or plasma chamber containing one or more gases, where an extension and concentration of the plasma can be achieved when the plasma extends past the exhaust of the plasma discharge chamber, to reach the article. In one embodiment of the invention, one or more gases are dissociated, which could include one or more inert gases and one or more reactive gases (e.g., air, or a oxygen-based or halogen-based gas) with or without other gases. The invention can be implemented in numerous ways, such as by a method, an apparatus, or a plasma system. Four aspects of the invention are described below.

A first aspect of the invention is directed to a method for treating one or more articles with a selectively extended and concentrated plasma generated from dissociating one or more gases. The method includes supplying one or more gases from a source to a first chamber; applying RF power to dissociate the one or more gases and create a plasma; withdrawing the dissociated one or more gases from the first chamber through a RF grounded pathway, wherein the RF grounded pathway selectively extends and concentrates a plasma in the RF grounded pathway; and supplying the dissociated one or more gases to a treatment chamber containing one or more articles.

A second aspect of the invention is directed to a method for treating one or more articles with a selectively extended and concentrated plasma generated by dissociating one or more gases. The method includes supplying one or more gases from a first source to a first chamber, applying RF power to dissociate one or more gases in the first source and create a first plasma, withdrawing the first plasma from the first chamber through a first RF grounded pathway and selectively extending and concentrating the first plasma with a first RF grounded pathway; supplying one or more gases from a second source to a second chamber for RF power to dissociate the one or more gases from the second source to create a second plasma; using a second RF grounded pathway to withdraw the second plasma from the second chamber and selectively extending and concentrating the second plasma with the second RF grounded pathway; and supplying the extended and concentrated first plasma from the first chamber and extended and concentrated second plasma from the second chamber to a treatment chamber containing one or more articles.

A third aspect of the invention is directed to an apparatus to dissociate one or more gases to produce a plasma. The apparatus includes a first chamber coupled to a source of one or more gases; one or more RF energy sources coupled to the first chamber; means for disassociating the one or more gases in the first chamber into a plasma; a RF grounded pathway to selectively extend and concentrate the plasma into an extended and concentrated plasma; a treatment chamber coupled to the first chamber through the RF grounded pathway to receive the extended and concentrated plasma, wherein the treatment chamber contains one or more articles.

A fourth aspect of the invention is directed to an apparatus to dissociate one or more gases to produce a plasma. The apparatus includes a first chamber with a first RF grounded pathway, coupled to a first source of one or more gases; a second chamber with a second RF grounded pathway, coupled to a second source of one or more gases; one or more RF energy sources coupled to the first chamber and the second chamber; means for dissociating the one or more gases into a first plasma in the first chamber and for dissociating one or more gases into a second plasma in the second chamber; at least one RF grounded pathway comprised of a conducting material to extend and concentrate at least one plasma from either the first chamber or from the second chamber; and a treatment chamber coupled to the first chamber and the second chamber, wherein the treatment chamber contains one or more articles.

These and other objects and advantages of the invention will become apparent to those skilled in the art from the following detailed description of the invention and the accompanying drawings.

DETAILED DESCRIPTION OF THE PREFERRED EMBODIMENTS

The invention provides a method, an apparatus, and a system to concentrate and extend a plasma. Various embodiments of the invention can be applied to biological applications, medical applications, chemical applications, electronic applications, and any other applications where plasma can be beneficially used.

Inductive coupling or capacitive coupling can be used to couple radio-frequency (RF) electromagnetic energy to one or more gases for dissociation and creation of plasma. In this specification, drawings, and claims, radio-frequency (RF) is defined as any frequency of electromagnetic energy where inductive or capacitive coupling to a plasma can be implemented.

In one embodiment, a plasma source is defined as a device that can partially ionize a gas or a mixture of gas at a reduced pressure. In one embodiment of the invention, the plasma produced can be a low temperature plasma, wherein the bulk gas temperature remain low (e.g., a few hundred degrees Celsius, more or less), while the electron temperature can be much higher (e.g., having a kinetic energy of a few hundred electron volts (eV), more or less).

What are Reactive Neutrals?

In one embodiment, the "radicals" (also called active neutrals, actives species, neutral species) have no electrical charge associated with them. The oxygen O radical, for example, can diffuse over a long distance (a few meters at 1 milliTorr) and still be chemically reactive.

Plasma Initiation Process:

The RF energy is transferred to the electrons. The electrons then partially dissociate and ionize the gas. In one embodiment of the invention operating at low power, dissociation generation of radicals occurs. A typical embodiment of the invention will convert un-reactive gas molecules into very reactive radicals. Most plasma surface chemistry is accomplished by radicals, such as the following examples (where "e–" represents an electron).

$$e\text{–}+O_2 => O+O+e\text{–} \tag{1}$$

$$e\text{–}+CF_4 => CF_3+F+e\text{–} \tag{2}$$

Ionization

Ionization of gas molecules will typically result in the production of ions and electrons, such as the following examples.

$$e\text{–}+O_2 => O_2^+ + 2e\text{–} \tag{3}$$

$$e\text{–}+Cl_2 => Cl_2^+ + 2e\text{–} \tag{4}$$

$$e\text{–}+Ar => Ar+2e\text{–} \tag{5}$$

Dissociative Ionization

Dissociative ionization can also occur as well in one collision.

$$e\text{–}+CF_4 => CF_3^+ + F + 2e\text{–} \tag{6}$$

$$e\text{–}+O_2 => O^+ + O + 2e\text{–} \tag{7}$$

As mentioned before, one goal of this invention is to increase the amount of reactants that reach the surface of an article located downstream from the plasma source into a vacuum chamber. One embodiment of the invention has two aspects. One aspect is to direct the reactant towards the surface of the article before they can diffuse into the whole chamber and become diluted (thus resulting in a lower reactant density). The second aspect is to extend the plasma downstream from the source to keep on transferring energy to the gas to keep the reactant energized farther away from the plasma source.

In one embodiment, another important consideration is the ability to operate over a large pressure range (hundreds of milliTorr to less than 1 milliTorr). The low pressure range (less than 1 milliTorr) provides a long mean free path (e.g., 5 centimeters at 1 milliTorr) needed if the distance from the plasma source to the article is greater than a few centimeters. In various embodiments, the lower the pressure, the farther the diffusion of reactants and the easier the implementation of electrostatic and electromagnetic coupling to the plasma downstream from the source will be, since the plasma will automatically have a tendency to expand downstream.

Typical design considerations for the RF grounded pathway in one embodiment would include:

1. The cross-sectional area is sized according to the size of the article, keeping in mind that as the cross-sectional area becomes larger, the concentration/density of the reactants becomes lower.
2. The length of the RF grounded pathway should be such that the amount of reactants diffusing away from the article (into the article's treatment chamber) is kept to a desirable amount.
3. The combination of cross-sectional area of the RF grounded pathway and the length of the RF grounded pathway determine the conductance of the RF grounded pathway and this also affects the diffusion of the reactants to the surface of the article in the treatment chamber. The diffusion also depends on the pressure regime at which the treatment chamber of the article operates (e.g., viscous flow, molecular flow or transition flow, and equivalent parameters).

Alternative embodiments are possible, but in one embodiment there are three specific goals for the materials in a RF grounded pathway:
1. The material should be a good conductor of the RF current for the frequency at which the plasma source operates.
2. The material exposed to the radicals must be inert to them and have a low recombination rate for the radicals.
3. The surface finish of the material should also be smooth to minimize the surface area of material at the molecular level.

For oxygen and a plasma radio-frequency set at 13.56 MHz, in one embodiment at least one or more of the following materials can be used in a RF grounded pathway:
1. Hard anodized aluminum with a water seal
2. Quartz
3. Nickel plated aluminum
4. Nickel plated stainless steel
5. $SiO_2$ coated metals which would otherwise be prone to oxidizing and thus depleting the oxygen O radicals.

For fluorine and a plasma radio-frequency set at 13.56 MHz, in one embodiment at least one or more of the following materials can be used in a RF grounded pathway:
1. Hard anodized aluminum with a water seal
2. Teflon coated hard anodized aluminum with a water seal
3. Ceramics
4. Teflon coated ceramic
5. Nickel plated aluminum
6. Nickel plated stainless steel
7. Quartz can only be used if the temperature is kept below approximately 40 Celsius, otherwise it will react and deplete the fluorine.

The working pressure is function of the distance between the plasma source and the article so what is important is the minimum pressure at which the system can work. In one embodiment of the invention, a typical useful plasma would have the following characteristics.
1. One typical useful plasma provides a high reactant density at low pressures (e.g., a pressure in the range of few milliTorr (e.g., less than 10 milliTorr) when the distance between the source and the article in the treatment chamber is large (e.g., 1 meter or more), in addition this type of plasma has a pressure range that is compatible with high vacuum systems and the mean free path and diffusion rate of the gas are very large in this pressure range. For example, 50 millimeters is the mean fee path for air at 1 milliTorr, as opposed to a mean free path of 0.5 millimeter at 0.1 Torr.
2. In one embodiment the source of plasma allows for extending the plasma by electrostatic or electromagnetic means into RF grounded pathways that are not frequency dependent, but sized to optimize the concentration of reactants at the surface of the article in the treatment chamber (e.g., the diffusion and density of reactant that is delivered by the source)

For a practical implementation, it should be noted that both electrostatic and electromagnetic couplings rely upon the presence of electrons to function. Therefore the lower the pressure, the easier it is to expand the plasma with electrons and ions present. For example, if in one embodiment, one operates in the pressure range of 1 milliTorr, then in this embodiment the length of the RF grounded pathway can be in the order of one meter and its diameter can be 2.5 centimeter (cm) to 5 cm to provide a good diffusion of the radicals. For embodiments of the invention with shorter lengths (e.g., 20 cm), a smaller diameter can be used (e.g., 2.5 cm), but here the dimensions must be chosen so that the conductance of the RF grounded pathway at the operating pressure is high enough to allow good diffusion of the radicals. In one embodiment, a 90 degree bend (or a chicane) in the RF grounded pathway can be included if one wants to prevent the photons from reaching the surface of the article, since without this bend the RF grounded pathway would provide a "direct line of sight" for the photons.

For the purpose of this invention, the article to be treated with plasma is considered to be far from the source when a large amount of reactive species can diffuse away from the surface of the article in the treatment chamber. Therefore, one need is to be able to transport and confine a large amount of active species from a plasma source to an article in the treatment chamber when the distance between the source and the article is large. In the prior art, a passive device is connected between the exhaust of the plasma source and the surface of the article in the treatment chamber. This prior art passive device takes the form of a tube (e.g., quartz tube for oxygen plasma or an equivalent) so that the active species will be confined by the inside volume of the tube, which is chosen to be much smaller than the volume of the treatment chamber containing the article. This also results in an increased density (concentration) of reactants at the surface of the article.

In the prior art, the tube is passive so it only provides a mechanical means of conducting the active species toward the article. But a passive tube does not extend the plasma towards the article(s). In contrast, various embodiments of the present invention, in addition to physically confining the active species to the inner volume of the RF grounded pathway, also provide various means of electrically coupling with the plasma (e.g., electrostatic coupling) to extend and concentrate the plasma and reduce the effect of reactive species lost during the physical transport of plasma from the plasma source to the surface of the article in the treatment chamber.

It should be noted that both the distance from one end of the RF grounded pathway to the exhaust of the plasma source and the distance of the opposite end of the RF grounded pathway to the surface of the article in the treatment chamber provide a means for controlling the amount of charge species reaching the surface of the article in the treatment chamber. It should also be noted that in preferred embodiments of the invention, the RF grounded pathway provides a RF ground return path. Therefore, in some embodiments of the invention, a conductive metal is included in the construction of the RF grounded pathway, but in alternative embodiments the RF grounded pathway can be coated with various materials (or an insert can be used) in order to minimize the loss of reactive neutrals on the inner surface of the RF grounded pathway.

Figure 1:
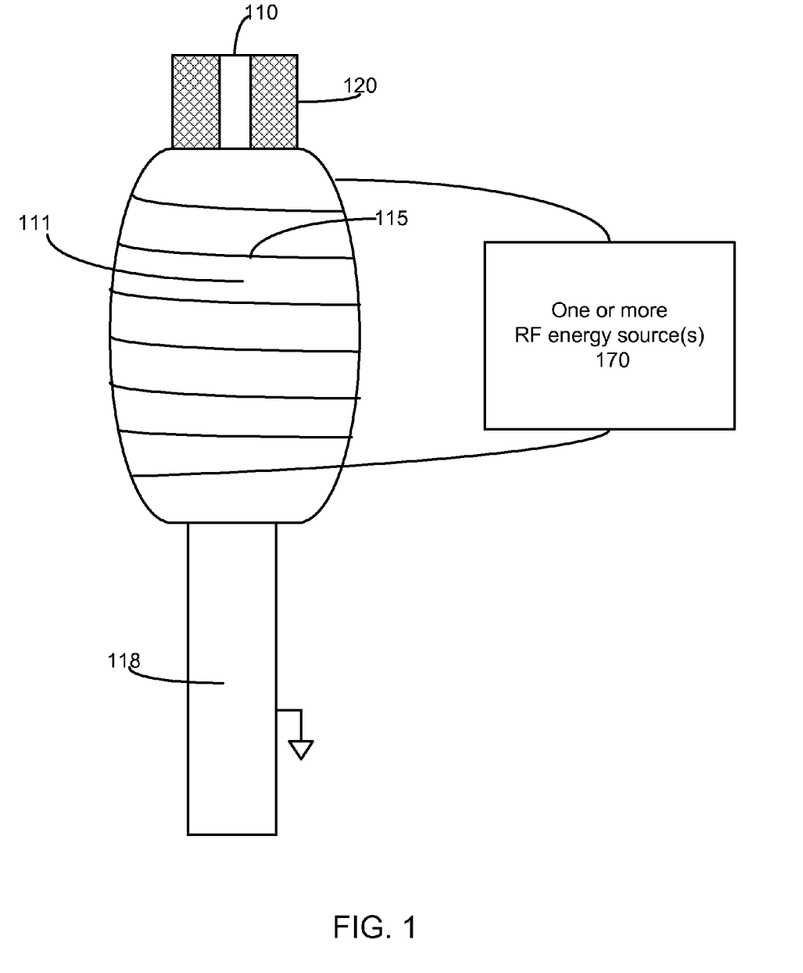
FIG. 1 illustrates an apparatus to generate, extend, and concentrate a plasma constructed in accordance with one embodiment of the invention.
Figure 3:
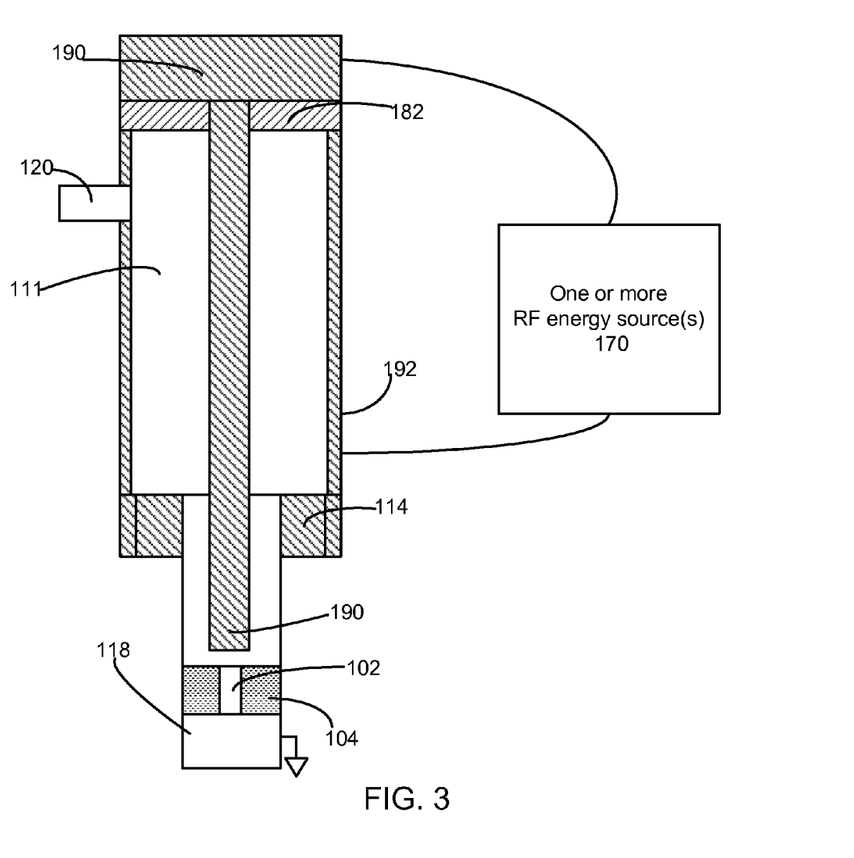
FIG. 3 illustrates an apparatus to generate, extend, and concentrate a plasma constructed in accordance with an alternative embodiment of the invention.

In FIG. 1, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a RF grounded pathway 118. RF grounded pathway 118 is grounded to extend and concentrate the plasma down the RF grounded pathway further than the plasma source alone would allow, since the RF field will diverge and terminate on the surfaces of the chamber containing the article(s). In one embodiment of the invention, the plasma source would include a constriction (as shown in FIG. 3), such as described in an earlier patent application by the same inventor, entitled "Higher Power Density Downstream Plasma," Ser. No. 10/781,226, filed on Feb. 18, 2004, and issued as U.S. Pat. No. 7,015,415 on Mar. 21, 2006, which is hereby incorporated by reference.

In various embodiments, the RF grounded pathway 118 can be fabricated from conducting metals (e.g., aluminum, stainless steel, copper, nickel-plated copper, or a combination, or an equivalent metal) to provide an electrical ground path for plasma inside the RF grounded pathway. In one embodiment, the RF grounded pathway comprises electrically conductive metal coatings (e.g., nickel-plated copper, copper, silver, aluminum, stainless steel gold, or various metal alloys or electrically conductive coatings, or equivalents), or includes coils including electrically conductive metal with a diameter ranging from one eighth of an inch (~0.3 centimeters) to one quarter of an inch (~0.6 centimeters). In another embodiment, an electrostatic rod (not shown) is inserted in the RF grounded pathway 118 for capacitive coupling with the plasma.

Figure 2:
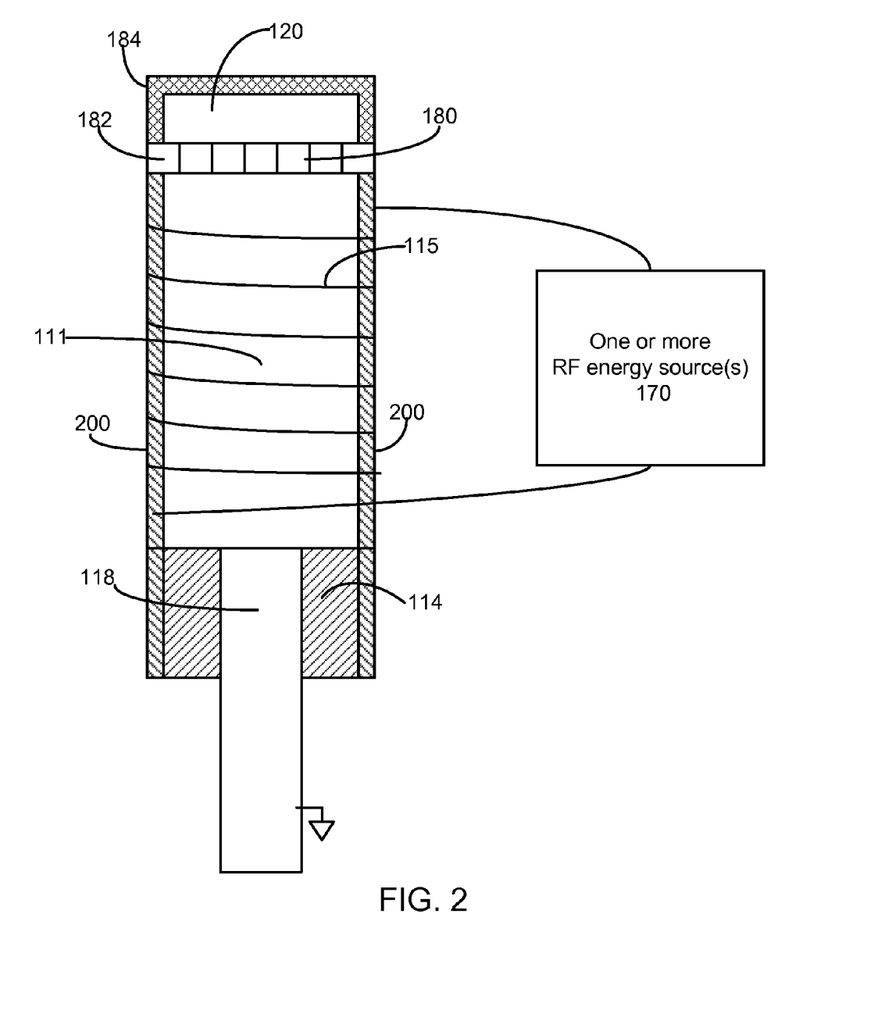
FIG. 2 illustrates an apparatus to generate, extend, and concentrate a plasma constructed in accordance with an alternative embodiment the invention.

In FIG. 2, a plasma generating chamber has a gas inlet 120 which supplies one or more gases to discharge chamber 111. A metal or dielectric material 184 encloses gas inlet 120 and a dielectric layer 182 has small openings (e.g., holes, slots, or equivalent perforations) 180 to prevent plasma expansion upstream from discharge chamber 111 through gas inlet 120. One or more RF energy sources 170 are coupled to inductor 115, which surrounds discharge chamber 111 and dissociates one or more gases passing through discharge chamber 111. The discharge chamber walls 200 may be made of various materials (e.g., a dielectric material such as, ceramic, glass, or an equivalent). Discharge chamber 111 is coupled to an article in a treatment chamber (not shown) by a RF grounded pathway 118. In various embodiments, the RF grounded pathway 118 can be fabricated from conducting metals (e.g., aluminum, stainless steel, copper, nickel-plated copper, or a combination, or an equivalent metal) to provide an electrical ground path for plasma inside the RF grounded pathway. RF grounded pathway 118 is grounded on the outside of the RF grounded pathway 118 to extend and concentrate the plasma. In another embodiment, an electrostatic rod (not shown) is inserted in RF grounded pathway 118 for capacitive coupling with the plasma.

Figure 4:
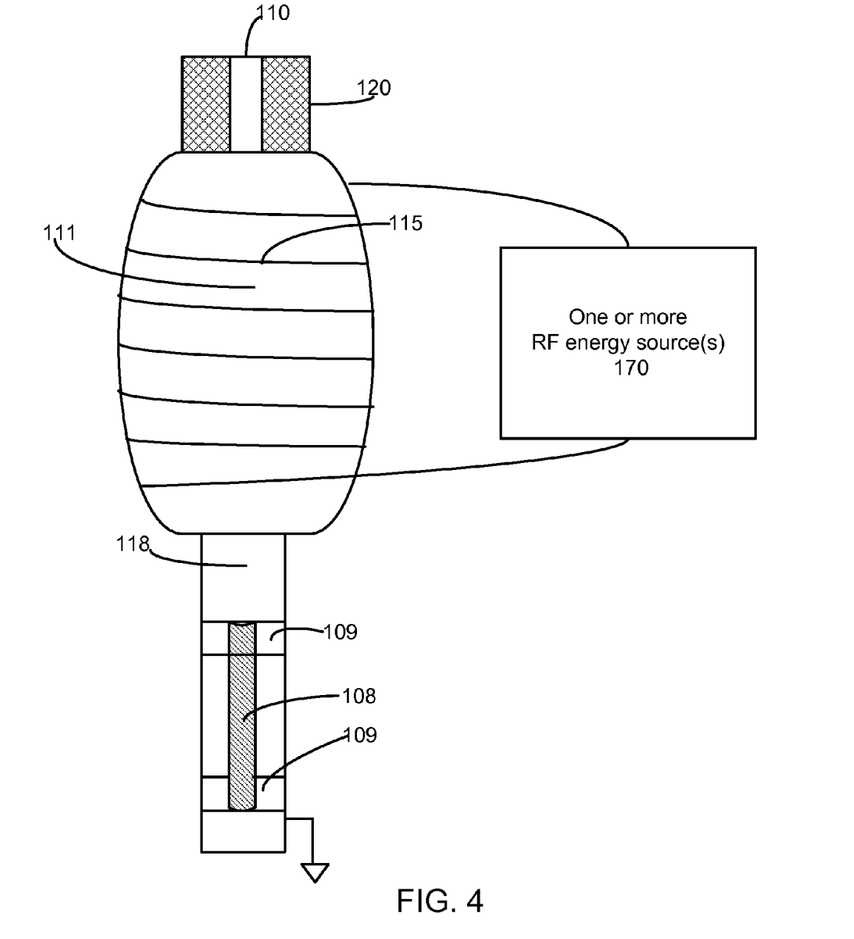
FIG. 4 illustrates an apparatus to generate, extend, and concentrate a plasma constructed in accordance with an alternative embodiment of the invention.

In FIG. 3, gas inlet 120 with a means to control backwards plasma expansion supplies one or more gases to discharge chamber 111. Discharge chamber 111 also has a dielectric layer 182 between the discharge chamber 111 and a first electrode 190. Both the first electrode 190 and a second electrode 192 are connected to one or more RF energy sources 170. One or more RF energy sources 170 provide the power to dissociate one or more gases passing through discharge chamber 111. The first electrode 190 can have shorter or longer lengths in different embodiments, but in this embodiment the first electrode 190 is extended so far as to partially reach inside a RF grounded pathway 118. Discharge chamber 111 is coupled to an article in a treatment chamber (not shown) by a RF grounded pathway 118. In various embodiments, the RF grounded pathway 118 can be fabricated from quartz or ceramic tubes coated with metal on the outside surface. This metal is then grounded to terminate the RF field to ground. In various embodiments, the RF grounded pathway 118 can be fabricated from conducting metals (e.g., aluminum, stainless steel, copper, nickel-plated copper, or a combination, or an equivalent metal) to provide an electrical ground path for plasma inside the RF grounded pathway. RF grounded pathway 118 is grounded on the outside of the RF grounded pathway 118 to selectively extend and concentrate the plasma inside the RF grounded pathway 118. In another embodiment, an electrostatic rod (as shown in FIG. 4) is inserted in RF grounded pathway 118 for capacitive coupling with the plasma. In one embodiment of the invention, the plasma source would include a constriction 102 in an insert 104, such as described in an earlier patent application by the same inventor, entitled "Higher Power Density Downstream Plasma," Ser. No. 10/781,226, filed on Feb. 18, 2004, and issued as U.S. Pat. No. 7,015,415 on Mar. 21, 2006, which is hereby incorporated by reference.

In FIG. 4, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a RF grounded pathway 118 with an electrostatic rod 108 and supports 109. This embodiment provides a ground path near the exhaust of the plasma source to terminate the RF leaking from the source as the plasma expands. In one embodiment, it can include a RF grounded pathway that is 5 centimeters to 25 centimeters long with a diameter ranging from 2.5 cm to 5.0 cm, including a hard anodized aluminum tube. In various embodiments, the RF grounded pathway 118 can be fabricated from conducting metals (e.g., aluminum, stainless steel, copper, nickel-plated copper, or a combination, or an equivalent metal) to provide an electrical ground path for plasma inside the RF grounded pathway 118. In one embodiment, the RF grounded pathway 118 can be coated on the inside surface with a material to provide a low recombination rate for radicals on the inside surface.

Figure 5:
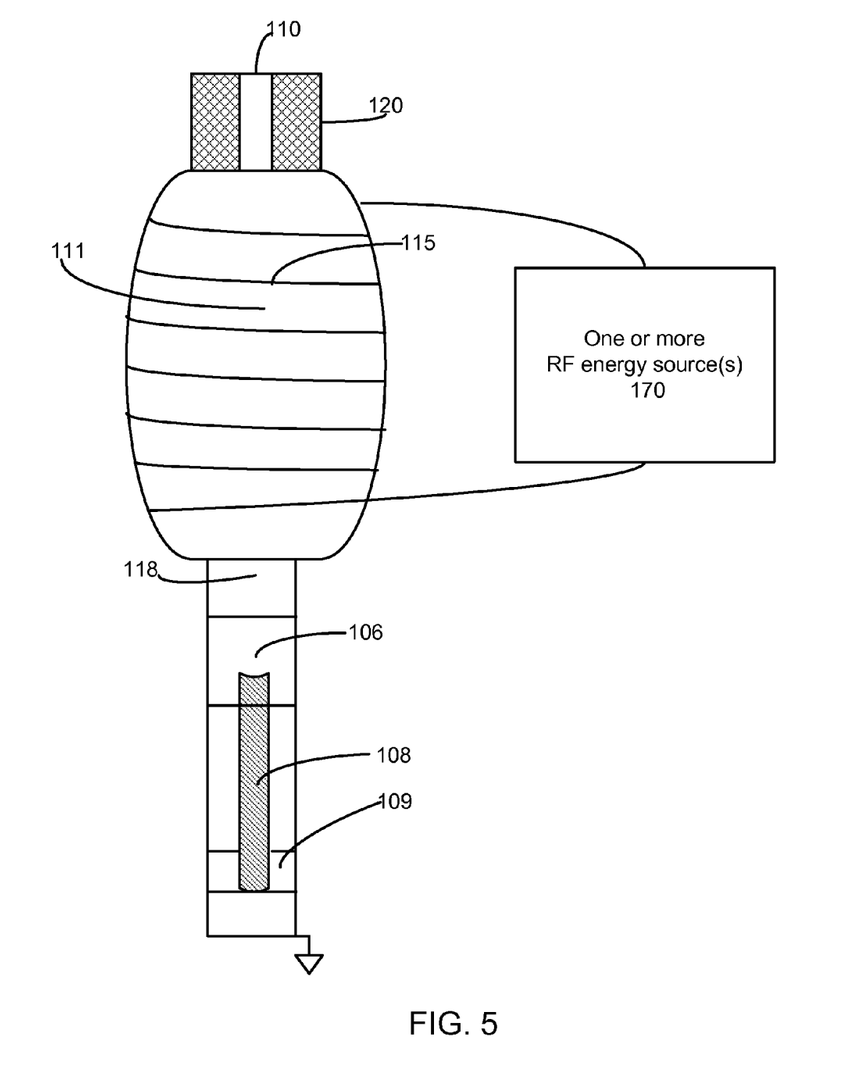
FIG. 5 illustrates an apparatus to generate, extend, and concentrate a plasma constructed in accordance with an alternative embodiment of the invention.

In FIG. 5, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a RF grounded pathway 118. This embodiment has an electrostatic rod 108 coupling to further increase the diffusion of the plasma toward the end of the RF grounded pathway 118. The RF grounded pathway 118 includes an electrostatic rod 108 with a pickup plate 106 and a support

109 inserted in the RF grounded pathway 118. The pickup plate 106 increases the capacitive coupling of the electrostatic rod 108 with the plasma.

In one embodiment, the length of the RF grounded pathway ranges from 25 cm to 100 cm, and has a diameter ranging from 2.5 cm to 5.0 cm. In one embodiment the electrostatic rod has a length ranging from 5 cm to 20 cm and a diameter of approximately 0.6 cm. In one embodiment, the RF grounded pathway 118 includes hard anodized aluminum with a water seal and a coating of Teflon® or silicon dioxide on the inside to prevent electrical contact between the pickup plate and the grounded aluminum RF grounded pathway 118. In various embodiments, the RF grounded pathway 118 and electrostatic rod 108 can be fabricated from conducting metals (e.g., aluminum, stainless steel, copper, nickel-plated copper, or a combination, or an equivalent metal) to provide a means to extend the plasma inside the RF grounded pathway 118.

In various embodiments, the pickup plate 106 and support 109 can be fabricated from one or more conducting metals (e.g., aluminum, stainless steel, copper, nickel-plated copper, or a combination, or an equivalent metal) and coated on the edges touching the inner surface of the RF grounded pathway 118 with an insulating material (e.g., ceramic, silicon dioxide, Teflon, or an equivalent) to prevent grounding the pickup plate 106 and support 109 to the conducting metal of the RF grounded pathway 118. In alternative embodiments, the pickup plate 106 and the support 109 can be fabricated from an insulating material (e.g., ceramic, silicon dioxide, Teflon, or an equivalent) and then selectively coated with a conducting metal as previously described, except for leaving insulating edges on the pickup plate 106 and the support 109 that touch the inner surface of the RF grounded pathway 118.

Figure 6:
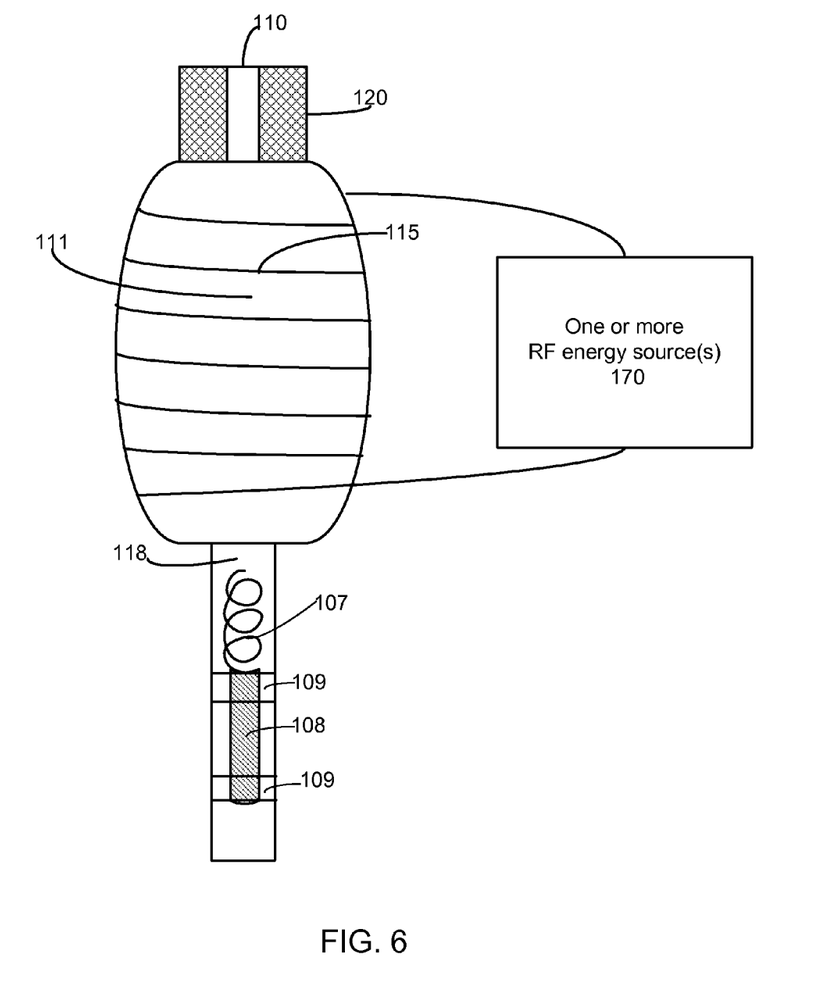
FIG. 6 illustrates an apparatus to generate, extend, and concentrate a plasma constructed in accordance with one embodiment of the invention.

In FIG. 6, a plasma generating discharge chamber includes a gas inlet 120 which supplies one or more gases to discharge chamber 111. Discharge chamber 111 also has a capillary tube 110 to prevent plasma expansion into gas inlet 120. One or more radio-frequency (RF) energy sources 170 are coupled to inductor 115, which surrounds discharge chamber 111 and dissociates one or more gases passing through discharge chamber 111, which may be made of various materials (e.g., a dielectric material or an equivalent). Discharge chamber 111 is coupled to an article in a treatment chamber (not shown) by a RF grounded pathway 118. In one embodiment, the length of the RF grounded pathway ranges from 25 cm to 100 cm, and has a diameter ranging from 2.5 cm to 5.0 cm. This embodiment provide an electromagnetic coupling to further increase the diffusion of the plasma toward the end of the RF grounded pathway. The RF grounded pathway includes an electrostatic rod 108 with supports 109 inserted in the RF grounded pathway 118, and a coil 107 for inductively coupling of the electrostatic rod 108 to the plasma. In one embodiment the electrostatic rod 108 is nickel plated copper and has a length ranging from 5 cm to 20 cm and a diameter of approximately 0.6 cm.

In one embodiment, the RF grounded pathway 118 includes hard anodized aluminum with a water seal and a coating of Teflon® or silicon dioxide on the inside to prevent electrical contact between the electrostatic rod 108 and the grounded RF grounded pathway 118. In one embodiment, the inner coil 107 has an outer diameter ~0.6 cm less than the inner diameter of the RF grounded pathway for ease of assembly. In various embodiments, the coil 107 itself includes an electrically conductive metal (e.g., nickel plated copper, copper, silver, aluminum, gold, or various metal alloys or electrically conductive coatings, or equivalents), with a diameter ranging from one eighth of an inch (~0.3 centimeters) to one quarter of an inch (~0.6 centimeters), with spacings in the turns of the coil of ~0.3 cm. Other embodiments can have a coil with alternative dimensions.

In various embodiments, the coil 107 and supports 109 can be fabricated from one or more conducting metals (e.g., aluminum, stainless steel, copper, nickel-plated copper, or a combination, or an equivalent metal) and coated on the edges touching the inner surface of the RF grounded pathway 118 with an insulating material (e.g., ceramic, silicon dioxide, Teflon, or an equivalent) to prevent grounding the supports 109 to the conducting metal of the RF grounded pathway 118. In alternative embodiments, the supports 109 can be fabricated from an insulating material (e.g., ceramic, silicon dioxide, Teflon, or an equivalent) and then selectively coated with a conducting metal as previously described, except for the edges of the supports 109 that touch the inner surface of the RF grounded pathway 118.

Figure 7:
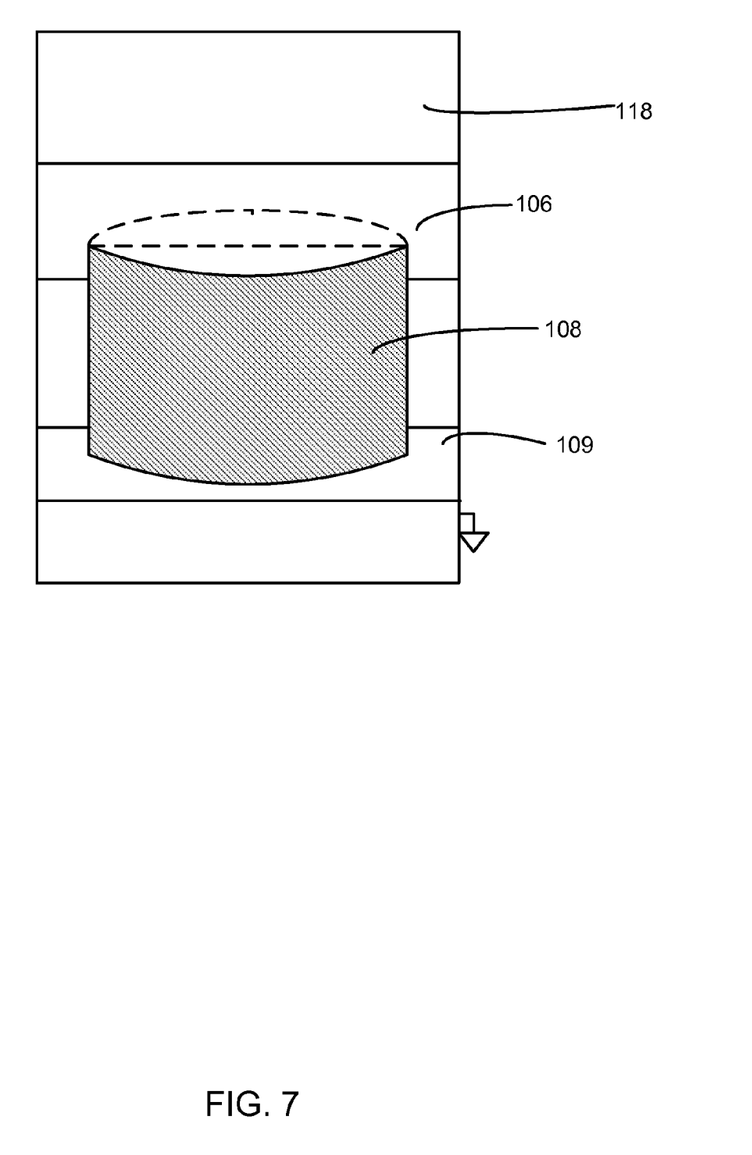
FIG. 7 illustrates an enlarged view of the RF grounded pathway and pickup plate support for an electrostatic rod in accordance with one embodiment of the invention.

FIG. 7 illustrates an enlarged view of the RF grounded pathway and pickup plate support for an electrostatic rod, in accordance to one embodiment of the invention. The one or more radio-frequency (RF) energy sources, inductor, discharge chamber are not shown. The RF grounded pathway 118 has an electrostatic rod 108 supported by a pickup plate 106 and a support 109. In one embodiment, the electrostatic rod 108 is slotted on each end, with a slot for the pickup plate 106 to be partially inserted and a slot for the support 109 to be inserted. In one embodiment, the electrostatic rod 108 is ~0.6 cm in diameter, but the diameter can be smaller or larger in alternative embodiments. In one embodiment, the pickup plate 106 is ~0.15 cm thick, but the pickup plate 106 can be thinner or thicker to fit thinner or thicker slots in the ends of the electrostatic rod in alternative embodiments. In a typical embodiment, the pickup plate 106 has a larger surface area for increasing the electrostatic coupling of the electrostatic rod 108 to the plasma than the surface of the support 109. The electrostatic rod 108 is RF insulated from the RF grounded pathway 118. In one embodiment an insulating material (e.g., silicon dioxide) is deposited inside the RF grounded pathway 118. In another embodiment the pickup plate comprises a dielectric material (e.g., quartz, ceramic, or an equivalent).

In various embodiments, the pickup plate 106 and support 109 can be fabricated from one or more conducting metals (e.g., aluminum, stainless steel, copper, nickel-plated copper, or a combination, or an equivalent metal) and coated on the edges touching the inner surface of the RF grounded pathway 118 with an insulating material (e.g., ceramic, silicon dioxide, Teflon, or an equivalent) to prevent grounding the pickup plate 106 to the conducting metal of the RF grounded pathway 118. In alternative embodiments, the pickup plate 106 and support 109 can be fabricated from an insulating material (e.g., ceramic, silicon dioxide, Teflon, or an equivalent) and then selectively coated with a conducting metal as previously described, except for the edges of the pickup plate 106 and support 109 that touch the inner surface of the RF grounded pathway 118.

Figure 8:
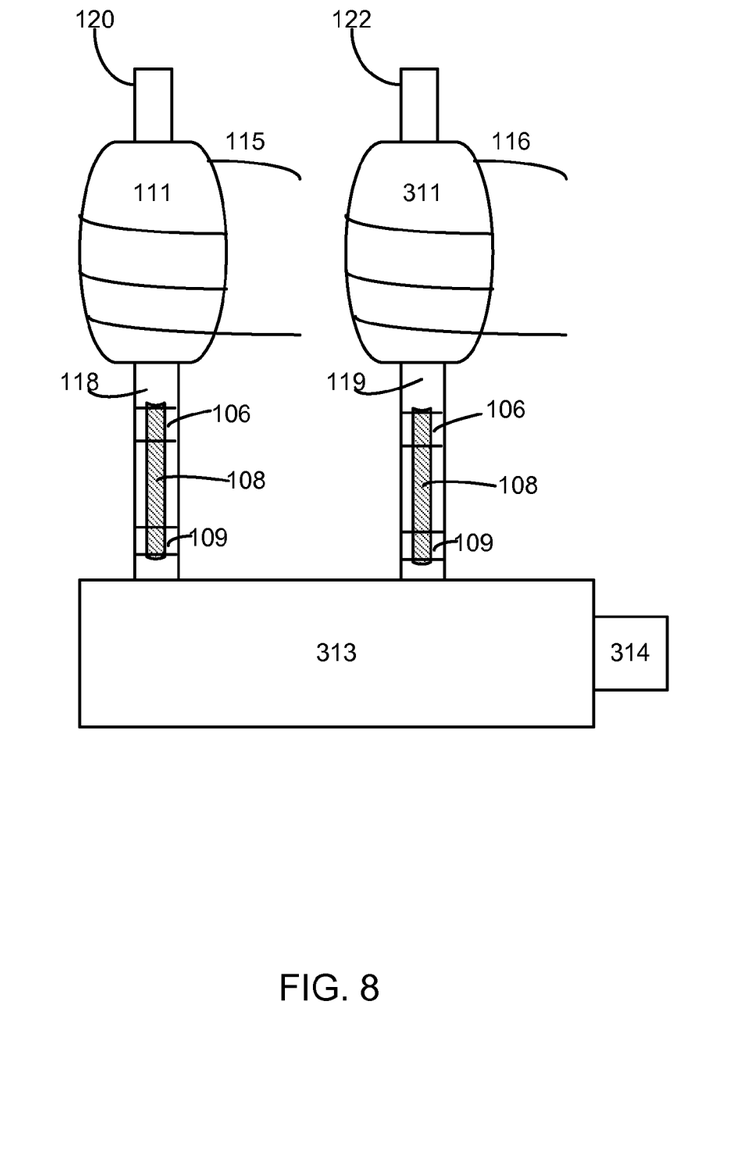
FIG. 8 illustrates an apparatus to generate, extend, and concentrate a plasma, in accordance with an alternative embodiment of the present invention, where two identical discharge chambers are coupled to a chamber for combining the plasmas from the discharge chambers.

When incompatible chamber materials and gas types occur (such as quartz and fluorine gas), multiple plasma sources can be used to dissociated each gas independently and the exhaust gas is combined to provide the desired mix of chemicals, such as in the next figure. FIG. 8 illustrates an embodiment of the invention in which the discharge chambers are essentially operating in parallel when inductors 115 and 116 are connected together to the same RF energy source(s). In an alternative embodiment, inductors 115 and 116 are connected to different RF energy source(s) to operate independently. In FIG. 8, gas inlets 120 and 122 provide one or more gases to discharge chambers 111 and 311 which are coupled to chamber 313 for combining the plasma from the discharge chambers 111 and 311 and supplying plasma to chamber 313. Inductor 115 surrounds discharge chamber 111 and dissociates the gas passing through chamber 111. Similarly, inductor 116 surrounds discharge chamber 311 and dissociates the gas passing through chamber 311. The RF power is supplied to inductors 115 and 116 by one or more RF energy sources (not shown). Discharge chamber 111 is coupled to chamber 313 by RF grounded pathway 118 and discharge chamber 311 is coupled to chamber 313 by RF grounded pathway 119. RF grounded pathway 118 is grounded on the outside of the RF grounded pathway 118 to selectively extend and concentrate the plasma. RF grounded pathway 119 is grounded on the outside of the RF grounded pathway 119 to selectively extend and concentrate the plasma.

Figure 9A:
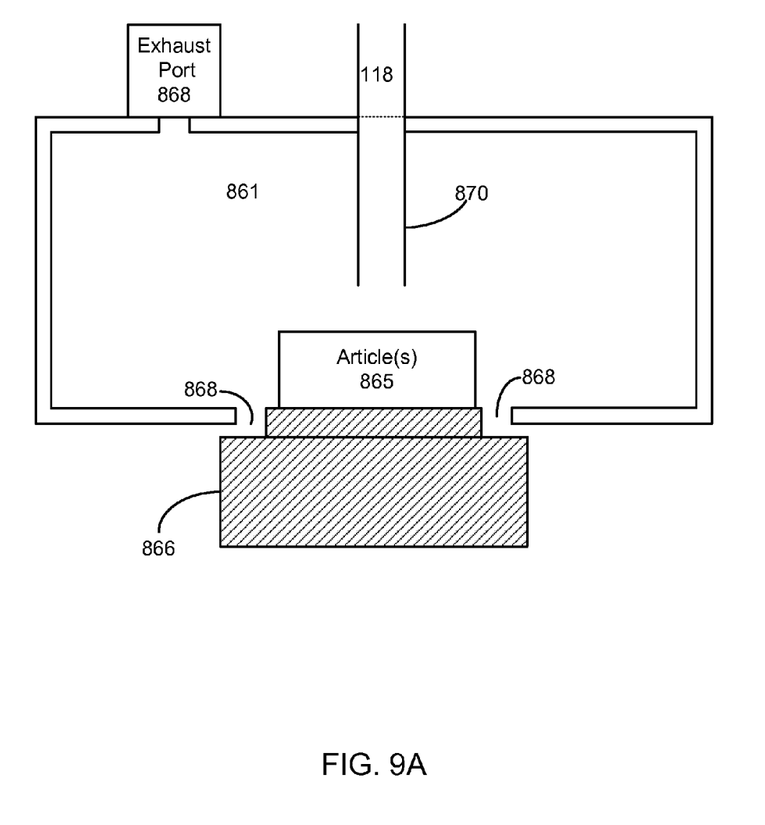
FIG. 9A illustrates a schematic cross-section of a treatment chamber for processing one or more articles, in accordance with one embodiment of the invention.
Figure 9B:
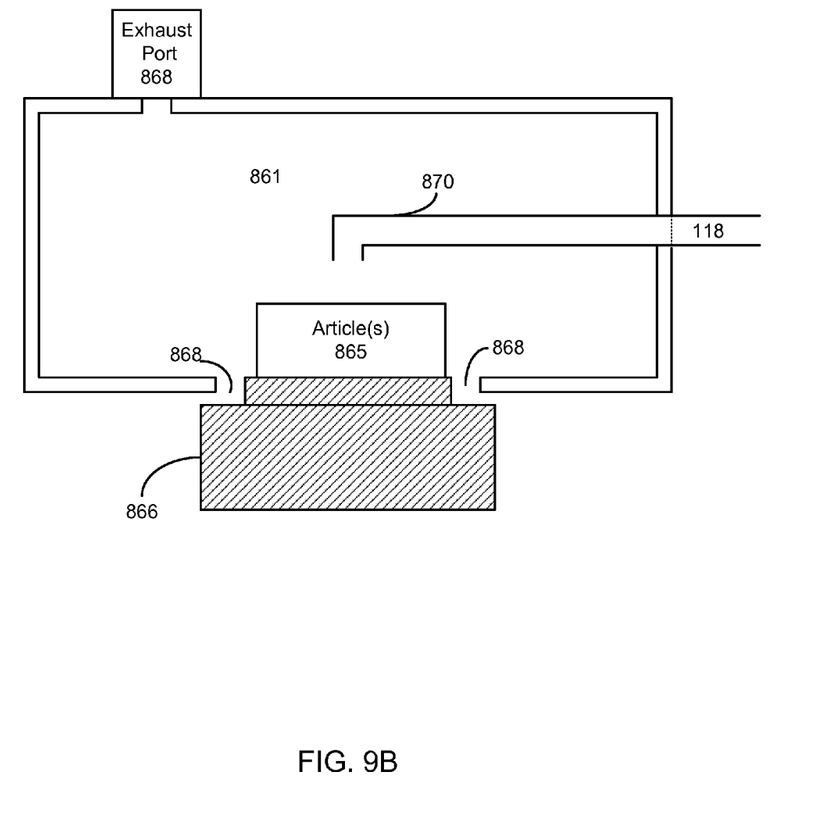
FIG. 9B illustrates a schematic cross-section of a treatment chamber for processing one or more articles, in accordance with another embodiment of the invention.

The reactive neutral species flow through RF grounded pathways 118 and 119 into chamber 313, where they mix and pass through port 314 to a treatment chamber, such as shown in FIGS. 9A and 9B. In an alternative embodiment, chamber 313 itself can be the treatment chamber containing the article(s). In various embodiments, the RF grounded pathways 118 and 119 can be independently fabricated. In another embodiment, an electrostatic rod (not shown) is inserted in RF grounded pathways 118 and/or 119 for capacitive coupling with the plasma.

In operation, a gas (e.g., an oxygen-based or halogen-based gas, or an equivalent gas) is supplied to discharge chamber 111 from a suitable source (not shown) and discharge chambers 111 and 311 are optionally supplied with one or more other gases from a suitable source (not shown). RF power from one or more RF energy sources (not shown) is coupled to the discharge chambers 111 and 311 by inductors 115 and 116.

FIG. 9A is a schematic cross-section of a treatment chamber 861 for processing one or more articles. Treatment chamber 861 is coupled to an RF grounded pathway 118 to receive one or more dissociated gases and distributing them over article(s) 865 on platen 866. RF grounded pathway extension 870 has no 90 degree elbow to block photons and directly directs a plasma onto the article 865. In an alternative embodiment of the invention, platen 866 and/or treatment chamber 861 are temperature-controlled to control the temperature of the article(s) 865. Gases are removed from treatment chamber 861 by a suitable vacuum pump (not shown) through one or more exhaust ports 868.

FIG. 9B is a schematic cross-section of a chamber 861 for processing one or more articles. Treatment chamber 861 is coupled to an RF grounded pathway 118 to receive one or more dissociated gases and distributing them uniformly over article(s) 865 on platen 866. RF grounded pathway extension 870 has at least one 90 degree elbow to block photons and directs a plasma onto the article 865. In an alternative embodiment of the invention, platen 866 and/or treatment chamber 861 are temperature-controlled to control the temperature of the article(s) 865. Gases are removed from treatment chamber 861 by a suitable vacuum pump (not shown) through one or more exhaust ports 868. In an alternative embodiment of the invention, treatment chamber 861 itself contains a plasma (not shown) generated directly in treatment chamber 861, in addition to plasma supplied from other chambers.

The invention thus provides apparatus for efficiently extending and concentrating one or more reactive gases in a plasma to provide concentrated plasma to at least one article, without contaminating the sources of the one or more reactive gases. In one embodiment of the invention, an increased density of plasma is created by the extension and concentration of active ions.

It will be apparent to those of skill in the art that various modifications can be made in terms of supplying the energy to dissociate the gases and produce plasma. As shown, RF power can be capacitively coupled, rather than inductively coupled, to one or more discharge chambers. Virtually any gas or mixture of gases can be dissociated at sufficient power densities in alternative embodiments of the invention.

Figure 10:
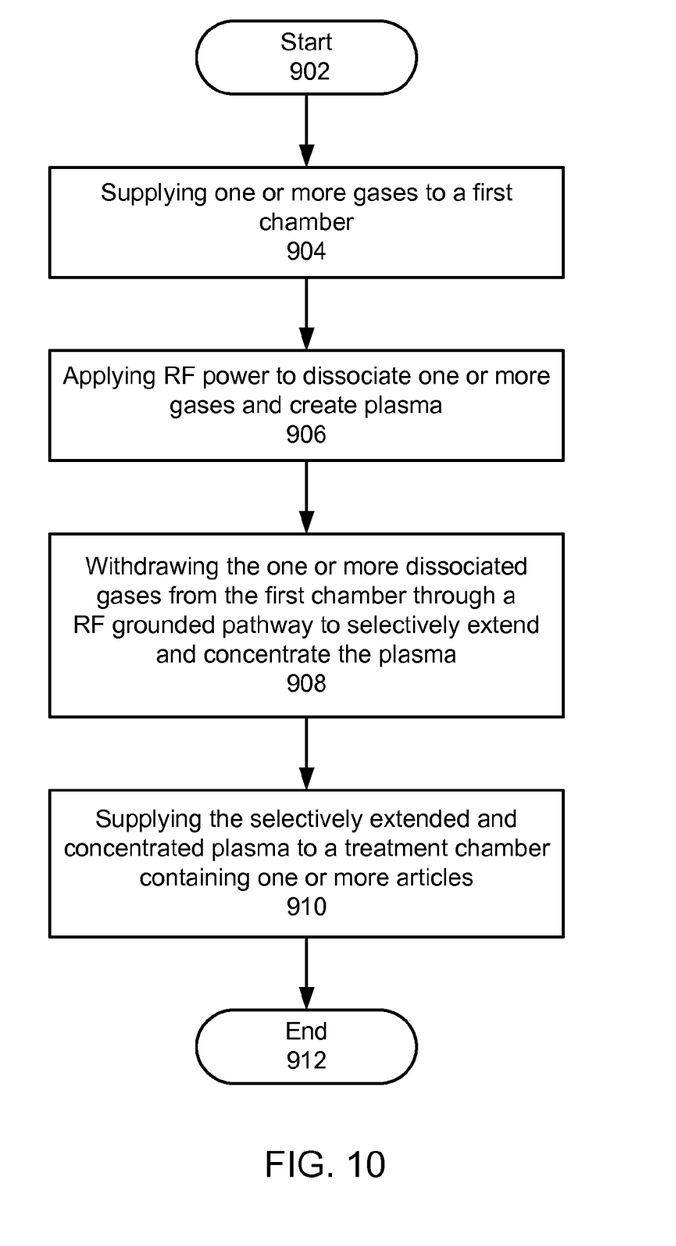
FIG. 10 illustrates a flowchart of a method to generate, extend, and concentrate a plasma, according to an alternative embodiment of the invention.

FIG. 10 illustrates a flowchart of a method to provide plasma, according to one embodiment of the invention. The sequence starts in operation 902. Operation 904 includes supplying one or more gases from a source to a first chamber. This operation in some embodiments of the invention would include using a means for controlling (i.e., reducing or preventing) expansion of plasma back through the source from the first chamber. Operation 906 includes applying RF power to dissociate one or more gases and create a plasma. Operation 908 includes withdrawing the one or more dissociated gases from the first chamber through a RF grounded pathway to selectively extend and concentrate the plasma at a pressure as low as 1 milliTorr or less. Operation 910 includes supplying the one or more dissociated gases to a treatment chamber containing one or more articles. The method ends in operation 912.

Figure 11:
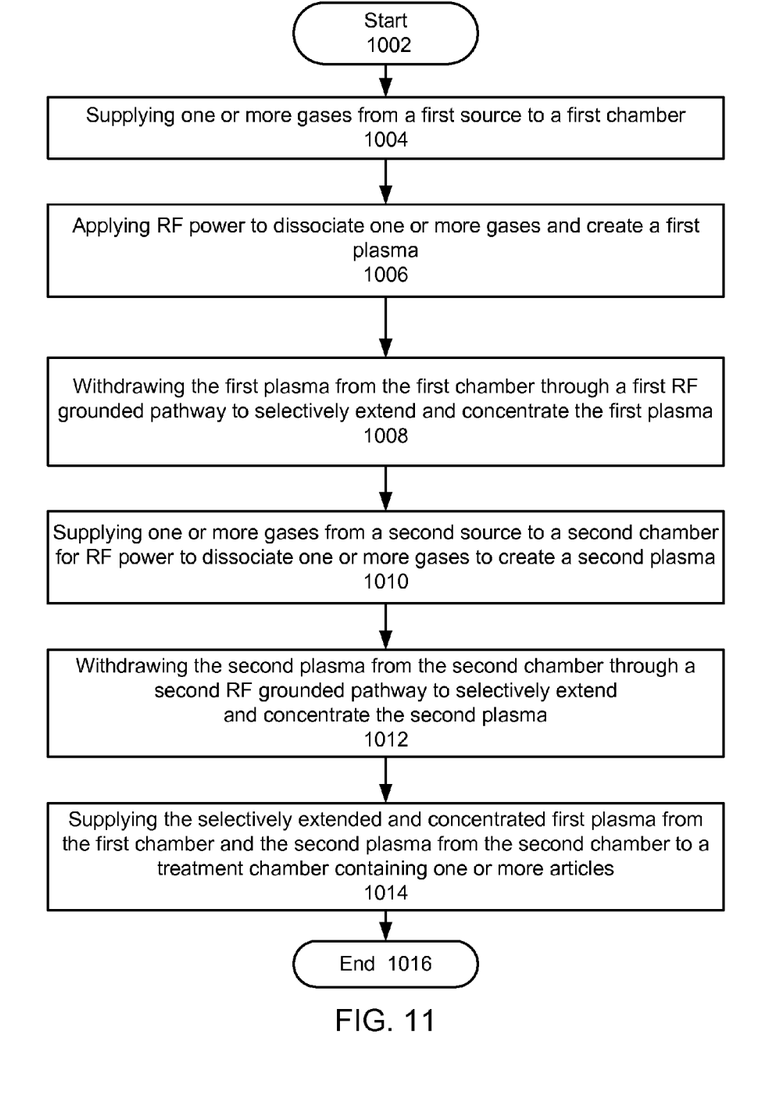
FIG. 11 illustrates a flowchart of a method to generate, extend and concentrate a plasma in parallel, according to an alternative embodiment of the invention.

FIG. 11 illustrates a flowchart of a method to provide plasma, according to an alternative embodiment of the invention. The sequence starts in operation 1002. Operation 1004 is next and includes supplying one or more gases from a first source to a first chamber. Operation 1006 includes applying RF power to dissociate one or more gases and create a first plasma. Operation 1008 includes withdrawing the first plasma from the first chamber through a first RF grounded pathway to selectively extend and concentrate the first plasma at a pressure as low as 1 milliTorr or less. Operation 1010 includes supplying one or more gases from a second source to a second chamber for RF power to dissociate one or more gases to create a second plasma. Operation 1012 includes withdrawing the second plasma from the second chamber through a second RF grounded pathway to selectively extend and concentrate the second plasma at a pressure as low as 1 milliTorr or less. Operation 1014 includes supplying the selectively extended and concentrated first plasma from the first chamber and the selectively extended and concentrated second plasma from the second chamber to a treatment chamber containing one or more articles. The method ends in operation 1016. In an alternative embodiment of the invention, an electrostatic rod (not shown) is inserted inside at least one RF grounded pathway to increase the capacitive coupling to the plasma. In an alternative embodiment, the first chamber and the second chamber are constructed differently and use either inductive coupling or capacitive coupling to apply RF power to the chambers. In an alternative embodiment, the first chamber and the second chamber are constructed identically.

In one embodiment, a constriction 102 is within an insert 104 that is removable, which can allow the constriction 102 to be disposable, easier to clean, and/or a different material than the material of the RF grounded pathway. The material used for constructing the constriction 102 can either be reactive or non-reactive with the plasma, as desired. In alternative embodiments of the invention the constriction 102 and insert 104 are a one-piece insert, including a reactive (i.e., reactive to the plasma) or non-reactive material.

In an alternative embodiment of the invention, one or more electrostatic rods (not shown) to increase the capacitive coupling to the plasma for extension and concentration. In an alternative embodiment, the first chamber and the second chamber are constructed differently and use either inductive coupling or capacitive coupling to apply RF power to the chambers. In an alternative embodiment, the first chamber and second chamber are constructed identically.

The exemplary embodiments described herein are for purposes of illustration and are not intended to be limiting. Therefore, those skilled in the art will recognize that other embodiments could be practiced without departing from the scope and spirit of the claims set forth below.

What is claimed is:

1. A method for treating one or more articles with a selectively extended and concentrated plasma generated from dissociating one or more gases, the method comprising:
   supplying one or more gases from a source to a first chamber;
   applying RF power to dissociate the one or more gases and create a plasma;
   withdrawing the dissociated one or more gases from the first chamber through at least one RF grounded pathway, wherein the at least one RF grounded pathway is electrically grounded and includes at least one conductive coating on a surface of the at least one RF grounded pathway and the at least one RF grounded pathway passively and selectively extends and concentrates the plasma in the at least one RF grounded pathway; and
   supplying the dissociated one or more gases to a treatment chamber containing one or more articles.

2. The method of claim 1, further comprising:
   applying RF power to one or more gases in an additional chamber having a second RF grounded pathway to dissociate the one or more gases from a second source into a second plasma, and withdrawing the second plasma through the second RF grounded pathway to selectively produce a second extended and concentrated plasma, and to supply the second extended and concentrated plasma to the treatment chamber containing one or more articles.

3. The method of claim 1, wherein at least one RF grounded pathway is comprised of a electrically conducting material to provide a ground path for a plasma to be extended and concentrated.

4. The method of claim 3, wherein at least one RF grounded pathway is comprised of a electrically conducting coating to extend and concentrate plasma from the at least one plasma source, wherein at least one RF grounded pathway includes a constriction.

5. The method of claim 1, wherein at least one RF grounded pathway has an electrostatic rod to help extend a plasma in the at least one RF grounded pathway.

6. The method of claim 1, wherein at least one RF grounded pathway has an electrostatic rod in contact with a pickup plate.

7. The method of claim 1, wherein at least one RF grounded pathway has an electrostatic rod in contact with a coil.

8. An apparatus for dissociating one or more gases to produce a plasma, the apparatus comprising:
   a first chamber coupled to a source of one or more gases,
   one or more RF energy sources coupled to the first chamber,
   means for dissociating the one or more gases in the first chamber into a plasma,
   a RF grounded pathway that is electrically grounded and includes at least one conductive coating on a surface of the RF grounded pathway to passively and selectively extend and concentrate the plasma into an extended and concentrated plasma, and
   a treatment chamber coupled to the first chamber through the RF grounded pathway to receive the extended and concentrated plasma, wherein the treatment chamber can contain one or more articles.

9. The apparatus of claim 8, wherein the means for dissociating the one or more gases includes inductively coupling RF energy to the one or more gases in the first chamber.

10. The apparatus of claim 8, wherein the means for dissociating the one or more gases includes a first electrode and a second electrode to capacitively couple RF energy to within the first chamber for dissociating the one or more gases.

11. The apparatus of claim 8, wherein the RF grounded pathway is comprised of a conducting material to extend and concentrate the plasma inside the RF grounded pathway.

12. The apparatus of claim 8, wherein the RF grounded pathway has an electrostatic rod inserted inside the RF grounded pathway.

13. The apparatus of claim 8, wherein the RF grounded pathway has an electrostatic rod with a pickup plate to increase the capacitive coupling between the electrostatic rod and a plasma inside the RF grounded pathway.

14. The apparatus of claim 8, wherein the RF grounded pathway has an electrostatic rod with a coil to increase the coupling between the electrostatic rod to a plasma that is to be extended and concentrated inside the RF grounded pathway.

15. The apparatus of claim 8, wherein the RF grounded pathway is comprised of an electrically conducting coating to extend and concentrate plasma from the at least one plasma source, wherein the RF grounded pathway includes a constriction inside the RF grounded pathway.

16. The apparatus of claim 8, wherein the pressure inside the RF grounded pathway can be 10 milliTorr or less.

17. An apparatus to dissociate one or more gases to produce plasma, the apparatus comprising:
   a first chamber with a first RF grounded pathway, wherein the first chamber is coupled to a first source of one or more gases,
   a second chamber with a second RF grounded pathway, wherein the second chamber is coupled to a second source of one or more gases,
   one or more RF energy sources coupled to the first chamber and the second chamber,
   means for dissociating the one or more gases from the first source of one or more gases into a first plasma in the first chamber,
   means for dissociating the one or more gases from the second source of one or more gases into a second plasma in the second chamber;
   at least one RF grounded pathway that is electrically grounded and includes at least one conductive coating on a surface of the at least one RF grounded pathway and the at least one RF grounded pathway is comprised of a conducting material to passively extend and concentrate at least one plasma from either the first chamber or from the second chamber; and
   a treatment chamber coupled to the first chamber and the second chamber, wherein the treatment chamber contains one or more articles.

18. The apparatus of claim 17, wherein at least one RF grounded pathway has an electrostatic rod inserted inside the at least one RF grounded pathway to extend and concentrate a plasma to treat one or more articles.

19. The apparatus of claim 17, wherein the first chamber and the second chamber supply the first plasma and the second plasma in parallel to the treatment chamber.

20. The apparatus of claim 17, wherein the pressure inside the treatment chamber can be less than 1 milliTorr.

* * * * *